United States Patent [19]
Locke et al.

[11] Patent Number: 5,411,736
[45] Date of Patent: May 2, 1995

[54] HYDROPHIC EXTRACTED NEEM OIL–A NOVEL INSECTICIDE

[75] Inventors: James C. Locke, Silver Spring; James F. Walter, Ashton; Hiram G. Larew, III, Hyattsville, all of Md.

[73] Assignee: W. R. Grace & Co.-Conn., New York, N.Y.

[21] Appl. No.: 89,084

[22] Filed: Jul. 9, 1993

Related U.S. Application Data

[60] Division of Ser. No. 947,867, Sep. 21, 1992, abandoned, which is a continuation-in-part of Ser. No. 456,762, Dec. 26, 1989, abandoned.

[51] Int. Cl.$^6$ ............................................. A01N 25/08
[52] U.S. Cl. ................................. 424/410; 424/195.1; 424/403; 424/404; 424/405; 424/406
[58] Field of Search ..................... 424/195.1, 410, 403, 424/404, 405, 406

[56] References Cited

U.S. PATENT DOCUMENTS 4,556,562  12/1985  Larson ............................. 424/195.1

OTHER PUBLICATIONS

"Activity of neem (Azadirachta Indica A Juss) Seed Kernel Extracts Against the Mustard Aphid, Lipaphis Erysimi," R. P. Singh, C. Devakumar and S. Dhingra, Phytoparasitica, 16(3), 225–230 (1988).

*Primary Examiner*—Thurman K. Page
*Assistant Examiner*—William E. Benston, Jr.
*Attorney, Agent, or Firm*—Beverly K. Johnson

[57] ABSTRACT

A novel insecticide derived from a neem seed extract comprising neem oil which is substantially free of azadirachtin, said neem oil being prepared by extracting dried, coarsely ground neem seeds with a non-polar, hydrophobic solvent to obtain a neem oil extract, and then removing the solvent to obtain the neem oil. These neem oil insecticides exhibit the ability to repel insects from plant surfaces and kill insect pests at various life stages.

7 Claims, No Drawings

HYDROPHIC EXTRACTED NEEM OIL–A NOVEL INSECTICIDE

This is a division of application Ser. No. 947,867, filed Sep. 21, 1992, now abandoned, which is a continuation-in-part application of U.S. patent application Ser. No. 456,762, filed Dec. 26, 1989, now abandoned.

FIELD OF THE INVENTION

This invention relates to novel insecticide and fungicide compositions derived from neem seeds, and more specifically to a novel insecticide and fungicide comprising a hydrophobic-solvent extracted neem oil. The neem oil extracts of the invention exhibit the ability to repel insects from plant surfaces, prevent fungal growth and kill insect and fungal pests at various life stages.

BACKGROUND OF THE INVENTION

The neem tree, a tropical evergreen, has been used for centuries as a source of pesticides to which insects have not developed a resistance. Various neem seed extracts, particularly the ones containing the hydrophilic, tetranortriterpenoid azadirachtin, are known to influence the feeding behavior, metamorphosis (insect growth regulating [IGR] effect), fecundity, and fitness of numerous insect species belonging to various orders.

It is known that neem oil, containing azadirachtin, may be mechanically pressed from neem seeds in the cold by using oil presses or may be extracted using alcohols or other solvents using Soxhlet apparatus. Small amounts of neem oil can be obtained by kneading neem seed powder by hand after adding some water (Schmutterer & Helip 1988). Thus the term 'neem oil' has been used to describe a variety of materials containing a mixture of both hydrophilic and hydrophobic extractables. The variety of extraction methods and resultant variety in composition of neem oil has led to great confusion as to the true properties of "neem oil". Khan and Wassilew (1986) tested the effect of their "neem oil" (prepared by aqueous extraction of neem kernels) on 14 common fungi, including *Trichophytonrubrum, T. violaceus, T. concentrichus, T. mentagophytes, Epidermophyton floccosum, Mierosporum citaneum, Scrophulariopsis brevicaulis, Geotrichum Candidum* and *Fusarium sp* and found that it did not inhibit fungal growth and, in fact, the neem oil itself actually contained several species of growing fungi. Yet an anonymous article (Anon. 1986) reported that "10% Neem oil diluted from its emulsifiable concentrate formulation" completely inhibited several species of fungi such as *Aspergillus niger, Fusarium moniliforme, Macrophomina phaseolina* and *Drechslera rostrata*. However, the specific details of this formulation were not provided.

Similarly, there are discrepancies in the literature as to the use of neem oil to control insects. Schmutterer and Hallpap (1986) showed that aqueous neem seed extracts are significantly superior to neem oil in repelling leaf mites (*Scrobipalpa ergasina*), leaf roller (*Phycita melogenu*) and leaf hopper (*Jacobiella facialna*). Mansour et al. (1986) report that the pentane extract of neem seeds was much more effective at controlling the spider mite *Tetranychus cinnabarinus* than were ethanol or methanol extracts, but surprisingly, the pentane extract was less effective at controlling the mite, *Phytoseiulus persimilis* than were the ethanol or methanol extracts.

Yamasaki et al showed that the tetranortriterpenoid, salannin, can be isolated from crude plant extracts, obtained from Indian neem seeds which are known to be high in salannin content, using hexane. The biological activity of the salannin extract is reported to be feeding deterency and growth inhibition when applied to chewing insects such as beetles and caterpillars.

This invention provides a novel neem oil extract that is substantially free of azadirachtin and yet is effective as both a fungicide and an insecticide, in particular as a foliar fungicide and insecticide.

It has now been discovered that under the process of this invention, a non-polar, hydrophobic-solvent extracted neem oil, substantially free of azadirachtin, possesses the ability to repel insects from plant surfaces, kill insects at various life stages in particular the egg and larval stages, and control the growth of serious fungal pathogens. This dual activity as both an insecticide and a fungicide in the absence of azadirachtin is novel and unique.

The insecticide and fungicidal activities of the hydrophobically extracted neem oil is unique and unexpected in view of the absence of any known active ingredients.

SUMMARY OF THE INVENTION

It is an object of this invention to provide a novel insecticide that repels insect pests from plant surfaces and kills insects at various life stages, in particular the egg and larval stages.

It is also an object of this invention to provide a novel fungicide that controls the growth of various fungi.

Another object of this invention is to provide natural insecticide and fungicide formulations derived from neem seed extracts for the protection of plants from various insect pests and fungi.

In accordance with the present invention, there have been provided certain novel insecticide and fungicide formulations derived from neem seed extracts, said formulations comprising non-polar hydrophobic-solvent extracted neem oil fractions, that are substantially free of azadirachtin.

DETAILED DESCRIPTION

As used herein, the term "insecticide" is intended to encompass insect repellents, larvacides, ovicides and the like. The term "insecticidally effective amount" or "fungicidally effective amount" is meant that dosage of active substance sufficient to exert the desired insecticidal or fungicidal activity.

Some active ingredients of the seeds and leaves of the tropical neem tree, *Azadirachtin indica*, particularly the tetranortriterpenoids azadirachtin and salannin, are known for their potent insecticidal activities. The present invention is directed to various insecticide and fungicide formulations prepared from non-polar hydrophobic solvent extracted neem oil which are substantially free of azadirachtin and salannin, and yet said formulations possess the ability to repel insect pests from plant surfaces, kill insect pests at various life stages, in particular the egg and larval stage, and control fungal pathogens. For purposes of this invention, the term "substantially free of azadirachtin" is used herein to indicate non-polar hydrophobic solvent extracted neem oil having less than 1 weight percent of azadirachtin, preferably less than 0.2 weight percent of azadirachtin, most preferably less than 0.06 weight percent of azadirachtin.

Neem seeds can be quite variable in size, shape and composition. Seeds from around the world can be as small and round as a pea and as large and long as a bean. Neem seeds consist of two parts, a shell that does not contain oil or insecticidal activity and the kernel which contains oil and azadirachtin. However, the composition of seeds collected from throughout the world varies considerably as shown in Table A. In particular we have found that oil derived from neem trees with high azadirachtin concentration is both insecticidal and fungicidal.

TABLE A

| Seeds Source | % Kernel in Seed | % Volatile | Content Oil % | AZAD mg/gsk* |
|---|---|---|---|---|
| Senegal (Pout) | 54 | 7 | 22 | 6.6 |
| India (Punjab) | 55 | 5.8 | 30 | 1.6 |
| Togo (Atkpame) | 57 | 7.3 | 27 | 4.5 |
| Haiti (Arcahie) | 51 | 12.0 | 19 | 2.7 |
| Ghana (Bawk) | 57 | 6.4 | 14 | 3.9 |

*gsk = gram seed kernel

The insecticide and fungicide formulations of this invention are prepared from neem oil which has been extracted from dried, coarsely ground neem seeds with a suitable non-polar, hydrophobic solvent. In accordance with this invention, dried neem seeds, typically containing about 5 to 15% water, are coarsely ground to about 5 mesh. The ground neem seeds are then extracted with a non-polar hydrophobic solvent to remove neem oil. It is preferred to use a significant excess of solvent ($\geq 3$ to 1 w/w) to obtain good yields. The solvent must be suitably hydrophobic to prevent excess water from contaminating the product. Water in the extract will cause azadirachtin to be extracted from the seeds and result in hydrolysis of the extract. After extraction, substantially all of the solvent is removed from the extract by low temperature evaporation, preferably by vacuum evaporation, to yield the neem oil product.

In the compositions and formulations of the invention, the neem oil may be used alone or mixed with conventional inert agronomically acceptable (i.e. plant compatible and/or insecticidally inert) or physiologically-compatible (depending upon the intended use of the insecticide) adjuvants such as surfactants, stabilizers, antifoam agents and antidrift agents may also be added. Examples of compositions and formulations according to the invention include aqueous suspensions and dispersions, oily dispersions, pastes, dusting powders, wettable powders, emulsifiable concentrates, flowables, granules, baits, invert emulsions, aerosol compositions and fumigating candles.

The compositions and formulations are prepared in a known manner to one skilled in the art, for example by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents.

Adhesives such as carboxymethylcellulose and natural and synthetic polymers in the form of powders, granules or latices, such as gum arabic, polyvinyl alcohol, polyvinyl cellulose, and polyvinyl acetate, can be used in the formulations to improve the adherence of this insecticide. Furthermore, a lubricant such as calcium stearate or magnesium stearate may be added to a wettable powder or to a mixture to be granulated.

The neem oil of the present invention may be employed alone and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific applications made therefrom such as solutions, emulsions, suspensions, powders, pastes, and granules which are thus ready for use.

In general, insecticidal and fungicidal formulations in accordance with this invention can be prepared by diluting the neem oil with about 5 to 50%, preferably 5 to 20% and most preferably 7 to 15%, by volume emulsifying surfactant and may optionally contain 0-1% PABA or other UV screening material. Suitable emulsifying surfactants include sorbitan esters, ethoxylated and propoxylated mono- and diglycerides, acetylated mono- or diglycerides, lactylated mono- or diglycerides, citric acid esters of mono- or diglycerides, sugar esters, polysorbates, poly-glycerol esters, and the like, and mixtures thereof. The preferred emulsifying surfactants are the polyoxyethylene derivatives of fatty acid partial esters of sorbital anhydrides which are sold under the name Tween 20, Tween 40, Tween 60 and Tween 80. Prior to final application, these insecticidal and fungicidal formulations are typically diluted with water.

For foliar application it has been observed that rates of 0.1 to 10%, preferably 0.25 to 3%, neem oil diluted in water are effective for control of insect pests and fungal diseases without unacceptable plant damage. Neem oil may also be used at various dilutions to control various pest and disease problems on turf, horticultural and agricultural crops as well as stored fruits and vegetables. The neem oil formulations have been shown to be effective at controlling such insect pests as Colorado Potato Beetle, Diamond Backed Moth, Whitefly, Mealy bug, Aphids, Hornworm, Lacebug, mites, fleas, ticks, mosquitoes and flies and the like. They are also effective at controlling fungi such as mildews, rusts, dollar spot, brown patch, black spots, botrytis, and the like. Furthermore, the neem oil can be used to control parasitic pests on mammals such as lice, ticks, scabies, as well as eczema and dermatitis. The neem oil of this invention is particularly useful to repel moths in a confined space, i.e., closets.

Suitable non-polar, hydrophobic solvents for use in extracting the neem oil from the ground neem seeds will include those solvents having high neem oil solubility and substantially no azadirachtin or water solubility. The preferred non-polar solvents include, but are not limited to, aliphatic hydrocarbons and halogenated aliphatic hydrocarbons such as pentane, hexane, heptane, octane, nonane, decane, isooctane, chloropentane, chlorohexane, and the like, and their isomers; petroleum distillates, petroleum ether, and the like; aromatics and substituted aromatics such as benzene, toluene, chlorobenzene, benzaldehyde, xylenes, and the like; and mixtures thereof. Various other non-polar solvents having the above characteristics are well known to those skilled in the art, and the choice of a particular solvent is not per se critical to the invention, provided that azadirachtin is substantially insoluble therein and neem oil has a high degree of solubility therein.

Without further elaboration, it is believed that one skilled in the art, using the preceding detailed description, can utilize the present invention to its fullest extent. The principles, preferred embodiments and modes of operation of the present invention have been described in the foregoing specification. The following examples are provided to illustrate the invention in accordance with the principles of this invention, but are not to be construed as limiting the invention in any way except as indicated in the appended claims. Variations and changes may be made by those skilled in the art without departing from the spirit of the invention. All parts and percentages are by weight unless otherwise indicated.

EXAMPLE 1

This example illustrates the effectiveness of the non-polar, hydrophobic solvent extracted neem oil formulations of this invention on newly laid or near-to-hatch greenhouse whitefly (*Trialeurodes vaporariorum*) eggs. Eighty (80) kgs of dried defruited neem seeds from Africa were ground in a cutting mill to about 10 mesh. The ground seeds were added to a 300 gallon agitated vessel together with 140 gallons (259 kgs) of hexane and agitated for 18 hours. The extracted seeds were then separated from the hexane-neem oil solution by centrifugation. The hexane-neem oil solution was transferred to a 500 ml jacketed agitated vessel where the solution was heated to 165° F. to remove the excess hexane. The recovered neem oil had a hexane content of <1% and contained about 0.01 weight percent of azadirachtin. The extracted neem oil was formulated into respective 1% and 3% solutions in 100 mls of water containing 1 drop of surfactant (Ivory TM Liquid). To test the effectiveness of these formulations, 25 potted chrysanthemum plants, cv. Iceberg, had all but 3 fully-expanded leaves removed. The plants were placed in a whitefly colony for 24 hours, removed, and sprayed with a water-mist to remove the adult whiteflies from the plants. The plants were divided into 5 groups of 5 and treated as follows:

Group 1) sprayed with water 0 days after exposure (DAE) to whiteflies,

Group 2) sprayed with 1% neem oil formulation 0 days after exposure to whiteflies, Group 3) sprayed with 3% neem oil formulation 0 days after exposure to whiteflies, Group 4) sprayed with 1% neem oil formulation 4 days after exposure to whiteflies, and Group 5) sprayed with 3% neem oil formulation 4 days after exposure to whiteflies.

The greenhouse whitefly eggs usually hatched 5–6 days after oviposition, thus the 4 DAE treatments were applied near the time of egg hatch. Once all the eggs had hatched on the control plants (those sprayed with water), the effectiveness of the oil fraction was assessed by counting the unhatched eggs and dead nymphs per leaf. The results were as follows:

TABLE 1

Effect of Neem Oil When Sprayed on New and 4-Day-Old Greenhouse Whitefly Eggs Laid on Chrysanthemums

| Treatment | Eggs* | Dead Nymphs* | % Mortality** |
|---|---|---|---|
| Water | 317ab | 2c | 0 |
| 1%, 0 DAE | 185b | 100bc | 54 |
| 3%, 0 DAE | 153b | 143b | 93 |
| 1%, 4 DAE | 198ab | 180b | 90 |
| 3%, 4 DAE | 360a | 358a | 99 |

*Values are means per 100 $cm^2$ leaf area. Means within trial followed by the same letter are not significantly different; DMRT, P = 0.05, N = 15 leaves.
**Number of dead nymphs divided by the number of eggs.

The extracted neem oil at both concentrations and exposure times caused significant nymphal mortality. It was observed that most nymphs died as they were emerging from the egg case. The extracted neem oil was most effective on the older eggs applied at a concentration of 3%.

EXAMPLE 2

This example illustrates the effectiveness of extracted neem oil as a repellant to adult *Bemisia tabaci* whiteflies when sprayed on chrysanthemum foliage. The extracted neem oil was prepared and diluted into 1% and 3% formulations according to Example 1. To test the effectiveness of these formulations, nine 3-week-old potted chrysanthemum plants cv. Iceberg, having all but 3 fully expanded leaves removed, were divided into three groups of 3 and treated as follows:

Group 1) sprayed with water,

Group 2) sprayed with 1% neem oil formulation,

Group 3) sprayed with 3% neem oil formulation, and then exposed to a colony of whiteflies for 24 hours. After exposure, the plants were cleaned of adult whiteflies and the number of eggs per leaf was determined. The results were as follows:

TABLE 2

Repellency of Neem Oils Against *Bemisia tabaci* on Chrysanthemums

| Treatment | Eggs* |
|---|---|
| Water | 110.0a |
| 1% | 18.0b |
| 3% | 0.0b |

*Values are means calculated per 100 $cm^2$ leaf area. Means followed by the same letter are not significantly different; DMRT, P = 0.05, N = 9 leaves.

The results show that extracted neem oil is effective at repelling Bemisia whiteflies at both concentrations.

EXAMPLE 3

This example illustrates the longevity of repellant action of hydrophobic solvent extracted neem oil when sprayed on chrysanthemum foliage cv. Iceberg. Repellency was quantified by counting the number of greenhouse whitefly (*Trialeurodes vaporariorum*) eggs laid on leaves. Neem oil formulations were prepared according to Example 1. Forty eight 3–4 week old chrysanthemum plants cv. Iceberg having all but 3 fully expanded leaves removed, were divided into three groups of 16 plants each and treated as follows:

Group 1) sprayed with water,

Group 2) sprayed with 1% neem oil formulation,

Group 3) sprayed with 3% neem oil formulation.

On the same day as spraying (Day 0) 4 plants from each group were placed in a whitefly colony for 24 hours. On days 3, 7 and 14, 4 more plants from each group were exposed to the whitefly colony for 24 hours. After each exposure, the number of eggs per 100 $cm^2$ of leaf area on the top 2 treated leaves were counted. The results were as follows:

TABLE 3

Neem Oils - Residual Effects

| | Mean No. Eggs/100 $cm^2$ Leaf Area* | | | |
|---|---|---|---|---|
| Treatment | Day 0 | Day 3 | Day 7 | Day 14 |
| Water | 506a | 844a | 405a | 72a |
| 1% | 69b | 107b | 14b | 39ab |
| 3% | 18c | 17b | 1b | 5b |

*Means in same column followed by the same letter are not significantly different; DMRT, P = 0.05, N = 8 leaves.

The extracted neem oil formulations repelled ovipositing *T. vaporariorum* for up to 14 days after spraying.

There were no clear differences in the level of repellency between the 1% and 3% concentration, or the time between treatment and exposure.

EXAMPLE 4

Control of Bean Rust by Extracted Neem Oil

Neem oil was extracted according to the procedure in Example 1. The extracted neem oil contained 0.01% azadirachtin and was mixed with water and diluted to 0.25, 0.5, and 1% and sprayed on the fully expanded primary leaves of beans cv. Pinto 111 until run off. The leaves were then inoculated with bean rust (*Uromyces phaseoli*) spores and placed in a dew chamber to allow infection. After approximately 16 hours the bean plants were removed from the dew chamber and placed in a greenhouse. After seven (7) days the number of rust pustules was counted. The results, in Table 4, show that the extracted neem oil is an effective foliar fungicide at these concentrations.

TABLE 4

| Treatment | Pustules/100 cm2* | % Control |
|---|---|---|
| Control | 1174.4 a | 0 |
| 0.25% | 220.0 b | 81.1 |
| 0.50% | 116.6 b | 90.2 |
| 1.00% | 114.2 b | 90.2 |

*Treatments with same letter are statistically similar; DMRT, P = 0.05, N = 6 leaves.

EXAMPLE 5

Effect of Extracted Neem Oil and Margosan-O ® Insecticide on the Repellency of Whiteflies Extracted neem oil as prepared in Example 1 was compared to Margosan-O ® insecticide containing the insect repellent azadirachtin. In these experiments 3 plants each were sprayed with water (control sample), a 2% solution of Margosan-O ® insecticide or a 2% solution of neem oil until run off. The plants were then placed in a chamber containing a colony of greenhouse whiteflies (Trialeurodes) for 2 hours. The plants were then removed from the chamber, the adults removed, and the number of eggs laid per cm2 of leaf area counted. The results presented in Table 5 show that extracted neem oil is a much better repellent than Margosan-O ® insecticide or the control.

TABLE 5

| Treatment Factor | Eggs laid/cm2 Area* | Repellency Factor |
|---|---|---|
| Control | 8.70 a | 0 |
| Margosan-O ® insecticide | 1.13 b | 7.7 |
| Extracted Neem Oil | 0.058 c | 150 |

EXAMPLE 6

Control of Mildew on Hydrangea

A solution of 2% non-polar, hydrophobic solvent extracted neem oil (0.052 weight percent of azadirachtin) in water was sprayed on 5 hydrangea plants growing in greenhouse. The treated plants and an equal number of untreated plants were exposed to the natural mildew microrganisms found in the greenhouse for 6 weeks. At the end of this period the leaves of the plants were examined for mildew infestation. The untreated plants had an average of 46% of their leaves infested while the treated plants had 1.7% infestation.

EXAMPLE 7

This example illustrates the potent ovicidal activity and repellent feeding deterrency of hydrophobic solvent extracts of neem seeds. Neem oil containing 0.026 weight percent azadirachtin was extracted according to the procedure in Example 1, and diluted with water and surfactant into 0.22%, 0.66% and 2.0% neem oil formulations. A series of tests were run on 6 types of insect eggs, both young and old, including: Colorado potato beetle, tomato hornworm, housefly, Hawthorn lacebug, two-spotted spider mite, and greenhouse whitefly. The eggs were sprayed with water (as a control) and the 3 above neem oil formulations, and the number of hatching eggs was determined. The results were as follows:

TABLE VII

Ovicidal Activity of Neem Oil

| Insect | Dose (%) | % Egg Mortality Young Eggs | Old Eggs |
|---|---|---|---|
| Colorado Potato Beetle | 0 | 8 | 13 |
|  | 0.22 | 81 | 9 |
| Tomato Hornworm | 0 | 8 | 16 |
|  | 0.22 | 11 | 26 |
|  | 0.66 | 46 | 42 |
|  | 2 | 90 | 77 |
| Hawthorn Lacebug | 0 | 26 | 33 |
|  | 0.22 | 30 | 39 |
|  | 0.66 | 32 | 41 |
|  | 2 | 75 | 69 |
| Two-Spotted Mite | 0 | 16 | 12 |
|  | 0.22 | 54 | 33 |
|  | 0.66 | 81 | 52 |
|  | 2 | 90 | 95 |
| Greenhouse Whitefly | 0 | 6 | 12 |
|  | 0.22 | 20* | 27* |
|  | 0.66 | 30* | 42* |
|  | 2 | 41* | 49* |

*All treated insects died after hatching.

As is clear from the above table, the 2% neem oil was effective at controlling hornworm, lacebugs, mites and whitefly eggs whether they were young or old. Young Colorado potato beetle eggs were effectively killed by 2% neem oil.

We claim:

1. A method for protecting a plant from insect pest infestation comprising:
   extracting neem oil from neem seeds using a non-polar, hydrophobic solvent having neem oil solubility and substantially no azadirachtin and water solubility; and
   contacting the plant with a neem oil formulation containing 0.1 to 10% of the hydrophobic extracted neem oil which is substantially free of azadirachtin, 0.005 to 5% of emulsifying surfactant and 0 to 99% water.

2. The method of claim 1 wherein the plant is contacted with the neem oil formulation by spraying.

3. The method of claim 1 wherein the plants are turf, horticultural or agricultural crops.

4. The method of claim 1 wherein the plant is contacted with a fungicidally effective amount of the neem formulation.

5. The method of claim 1 wherein the neem oil formulation contains from 0.1 to 10% neem oil, 0.005 to 5% emulsifying surfactant and 0 to 99% water.

6. The method of claim 1 wherein the neem oil formulation contains from about 0.25 to about 3% neem oil.

7. The method of claim 1 wherein the insect pest from which the neem oil formulation protects the plant is selected from the group consisting of Colorado Potato beetle, Diamond Backed Moth, Whiteflies, leafminers, aphids, mealybug, hornworm, lacebug, mites, fleas, ticks, mosquitoes, and flies.

* * * * *